United States Patent
Weder

(10) Patent No.: US 6,691,457 B2
(45) Date of Patent: *Feb. 17, 2004

(54) FLORAL PACKAGING MATERIAL HAVING GREAT MASTERS PRINTS THEREON

(75) Inventor: Donald E. Weder, Highland, IL (US)

(73) Assignee: Southpac Trust International, Inc., Highland, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/266,192

(22) Filed: Oct. 4, 2002

(65) Prior Publication Data

US 2003/0029086 A1 Feb. 13, 2003

Related U.S. Application Data

(60) Continuation of application No. 09/643,482, filed on Aug. 22, 2000, now Pat. No. 6,510,650, which is a continuation-in-part of application No. 09/151,789, filed on Sep. 11, 1998, now abandoned, which is a continuation-in-part of application No. 08/967,706, filed on Nov. 10, 1997, now Pat. No. 5,839,255, which is a continuation of application No. 08/821,012, filed on Mar. 19, 1997, now Pat. No. 5,720,152, which is a division of application No. 08/477,003, filed on Jun. 7, 1995, now Pat. No. 5,661,951.

(51) Int. Cl.[7] .................................................. A01G 9/02
(52) U.S. Cl. .......................................................... 47/72
(58) Field of Search .................................. 47/72; 53/397

(56) References Cited

U.S. PATENT DOCUMENTS

| | | | |
|---|---|---|---|
| 2,845,735 A * | 8/1958 | Werner | 47/72 |
| 4,216,620 A | 8/1980 | Weder et al. | |
| 5,073,161 A | 12/1991 | Weder et al. | |
| 5,076,874 A | 12/1991 | Weder | |
| 5,120,382 A | 6/1992 | Weder | |
| 5,228,934 A | 7/1993 | Weder et al. | |
| 5,307,606 A | 5/1994 | Weder | |
| 5,388,386 A | 2/1995 | Weder | |
| 5,388,695 A * | 2/1995 | Gilbert | 206/423 |
| 5,443,670 A | 8/1995 | Landau | |
| 5,448,875 A | 9/1995 | Weder | |
| 5,493,809 A | 2/1996 | Weder et al. | |
| 5,501,039 A | 3/1996 | Weder et al. | |
| 5,572,851 A | 11/1996 | Weder | |
| 5,625,979 A | 5/1997 | Weder | |
| 5,647,168 A * | 7/1997 | Gilbert | 47/72 |
| 5,661,951 A * | 9/1997 | Weder | 53/397 |
| 5,715,588 A * | 2/1998 | Weder et al. | 29/469.5 |
| 5,720,152 A * | 2/1998 | Weder | 53/397 |
| 5,727,363 A | 3/1998 | Weder | |
| 5,752,360 A | 5/1998 | Weder | |
| 6,510,650 B1 * | 1/2003 | Weder | 47/72 |

OTHER PUBLICATIONS

Speed Covers ® Brochure—The Simple Solution For Those Peak Volume Periods, Highland Supply Corporation, ©1989, 4 pages.
Speed Sheets and Speed Rolls, Brochure, Highland Supply Corporation, ©1990, 2 pages.
Photo of Monet Paintings Gift Wrap Paper found @ www.DoverPublications.com.

(List continued on next page.)

Primary Examiner—Charles T. Jordan
Assistant Examiner—Francis T. Palo
(74) Attorney, Agent, or Firm—Dunlap, Codding & Rogers, P.C.

(57) ABSTRACT

An apparatus and method are disclosed for forming a decorative covering about a flower pot or a floral grouping from a sheet of material, the sheet of material having printed thereon a graphic image that is prominently displayed on a selected portion of the decorative covering. The graphic image may be a masterpiece of art produced by one of the Great Masters of the Renaissance, at least a portion of a musical score, or combinations thereof.

15 Claims, 8 Drawing Sheets

OTHER PUBLICATIONS

Photo of Picasso Paintings Gift Wrap Paper found @ www.DoverPublications.com.

Photo of Van Gogh Paintings Gift Wrap Paper found @ www.DoverPublications.com.

Photo of Matisse Paintings Gift Wrap Paper found @ www.DoverPublications.com.

Photo of Impressionists Paintings Gift Wrap Paper found @ www.DoverPublications.com.

Web Page illustrating painting gift wrap paper for purchase @ http://store.doverpublications.com/0486408396.html.

* cited by examiner

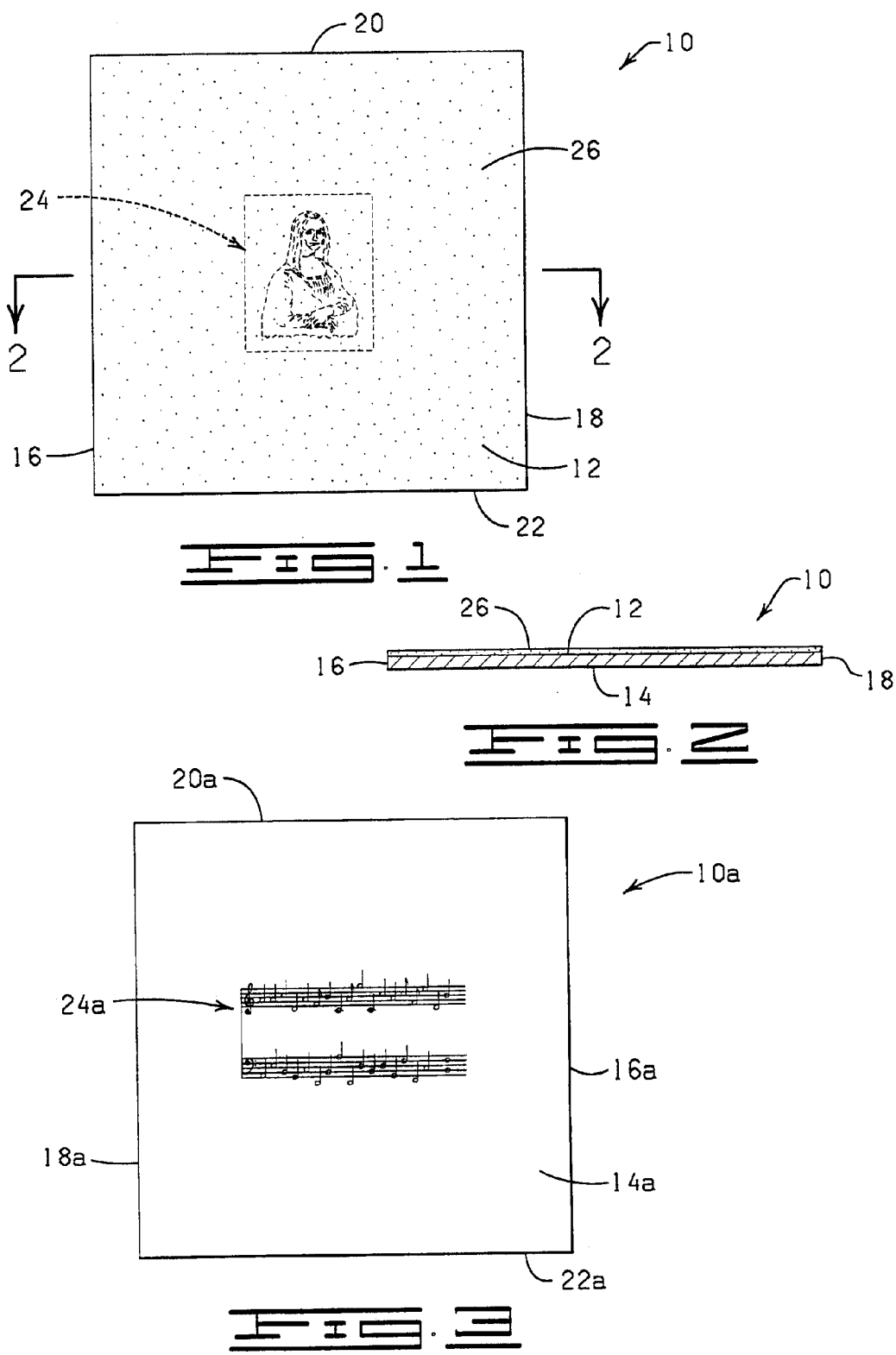

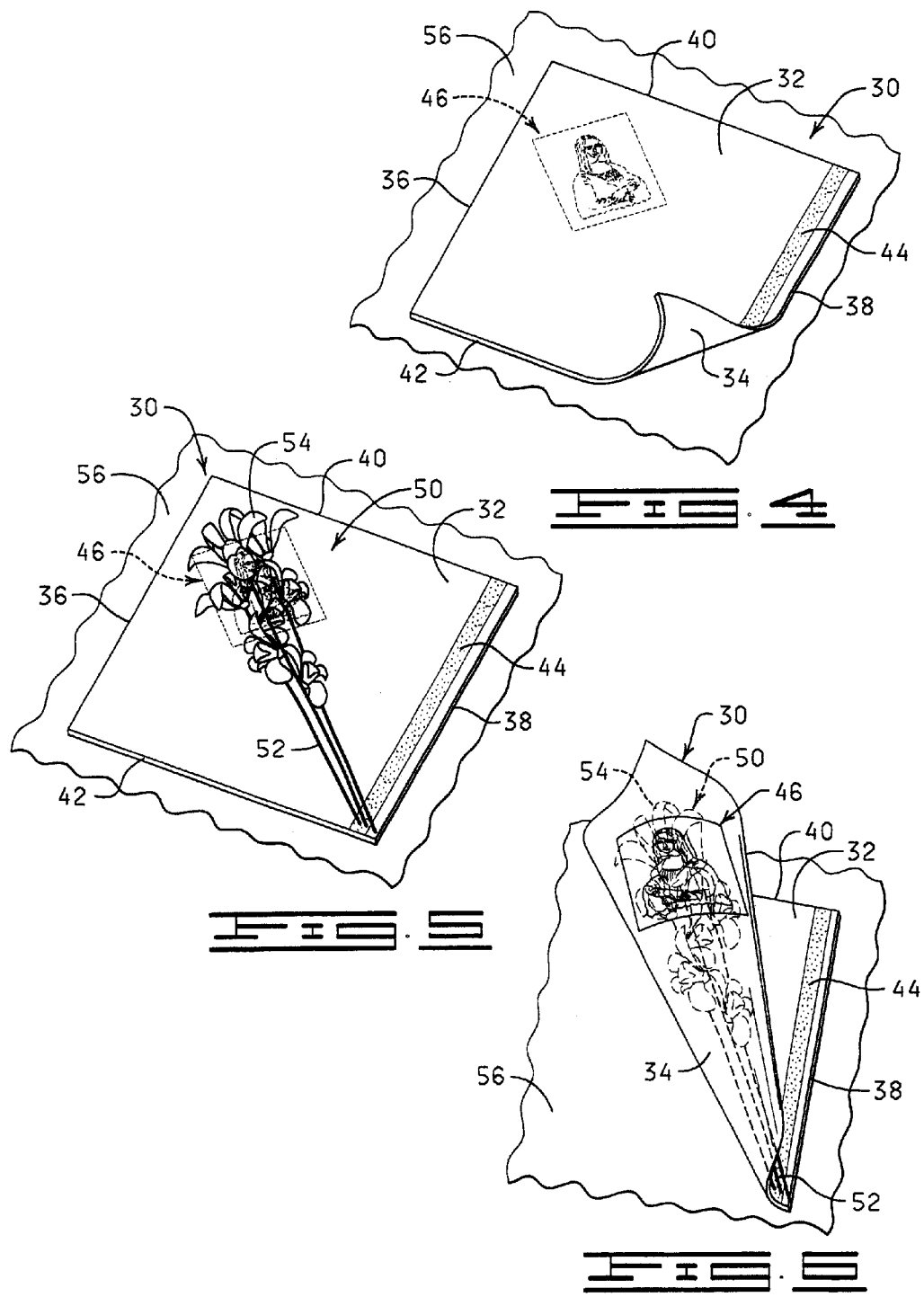

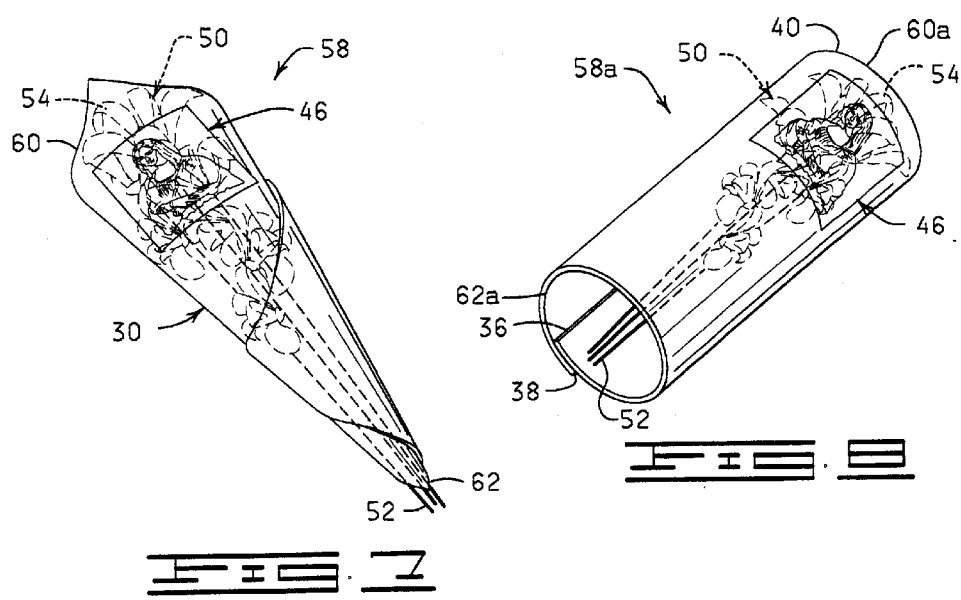
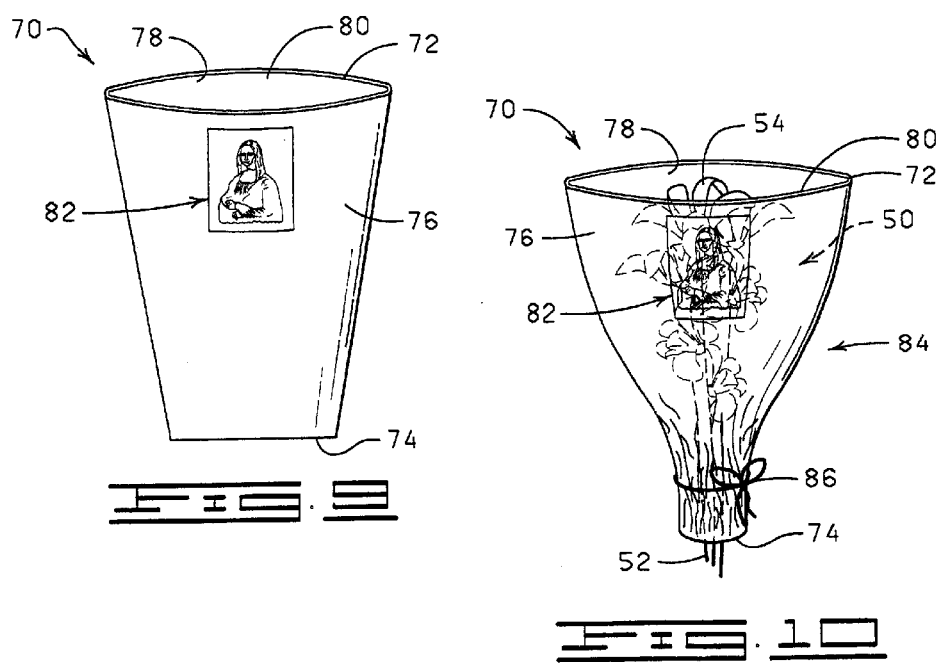

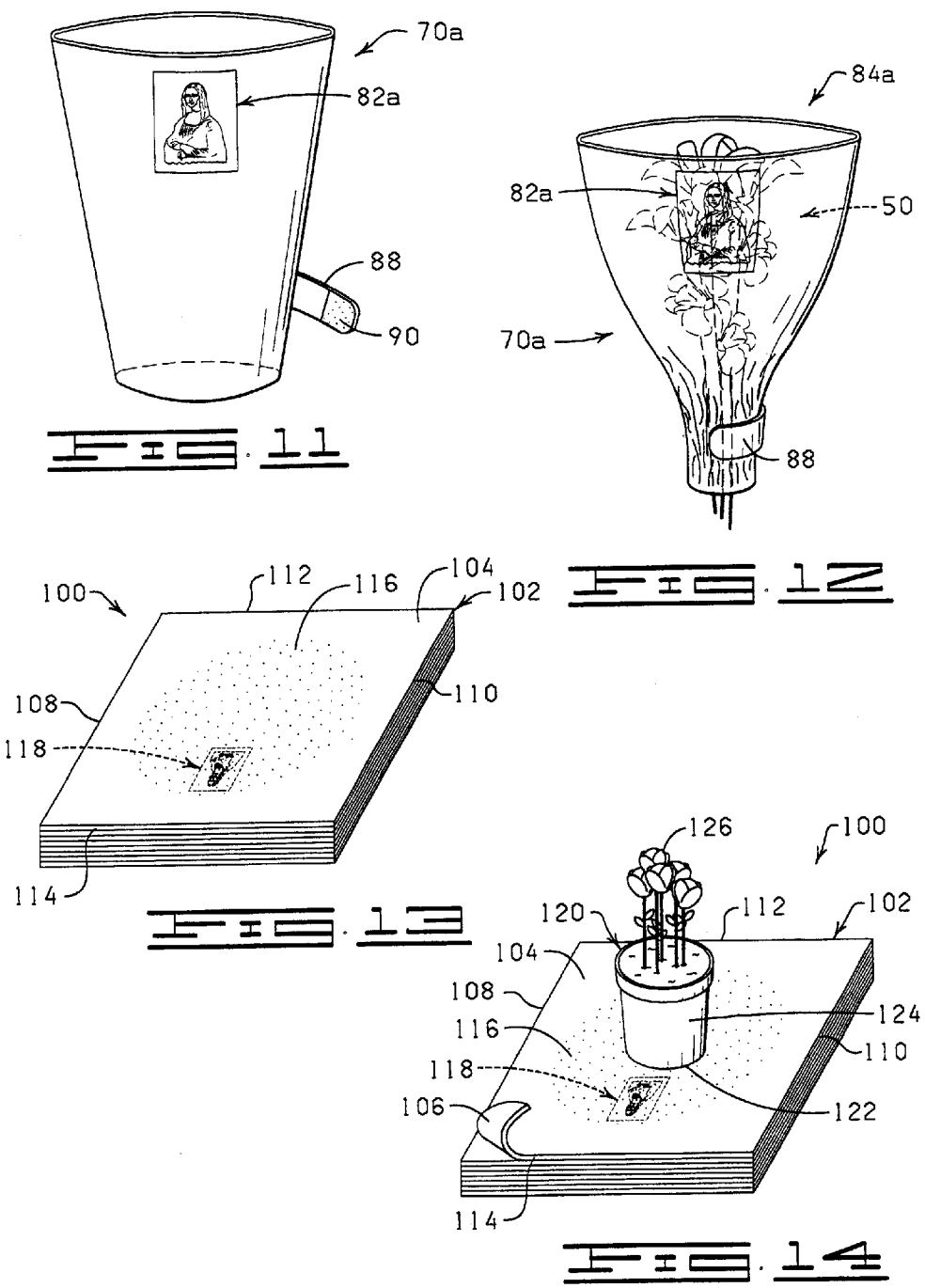

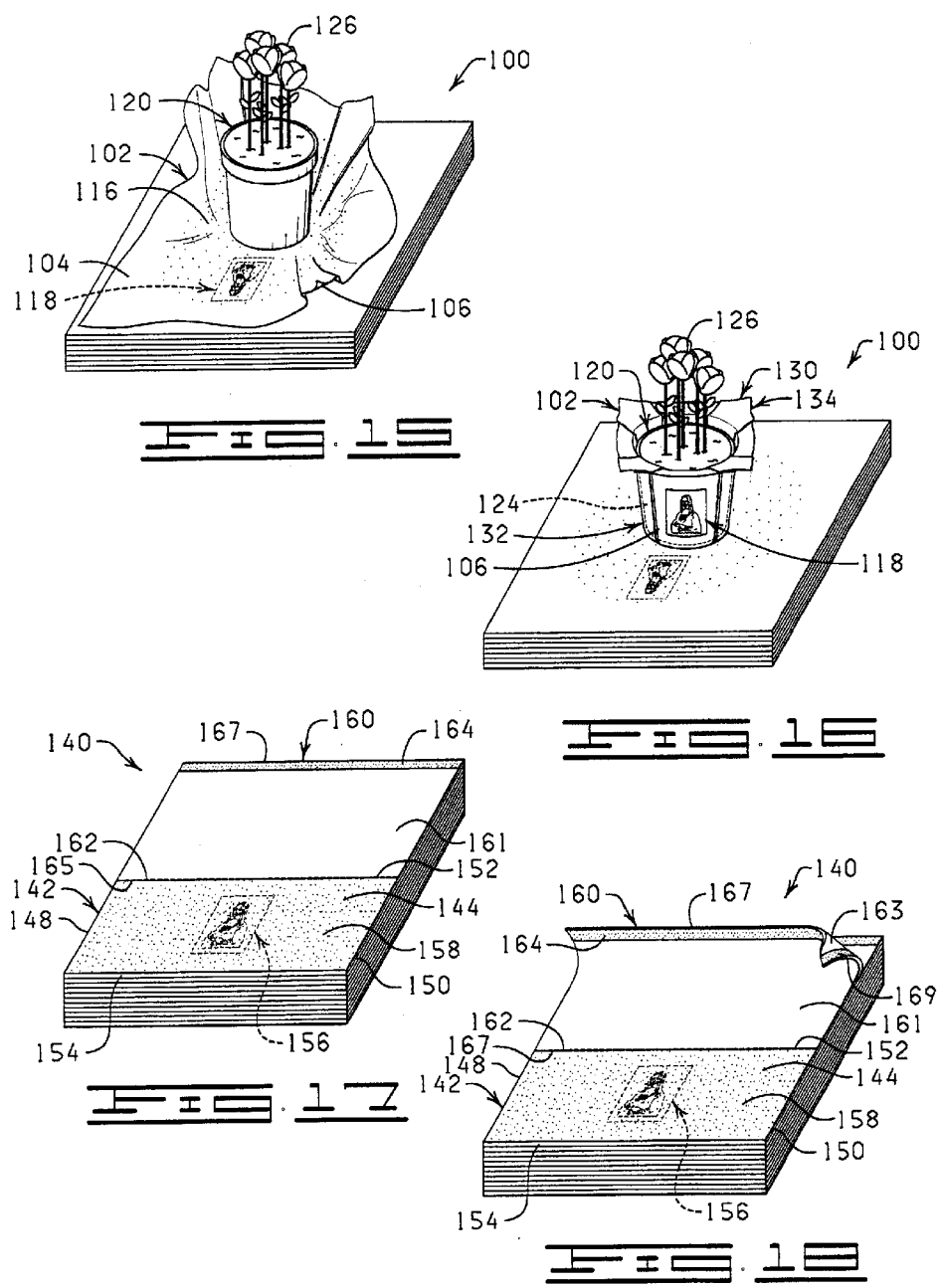

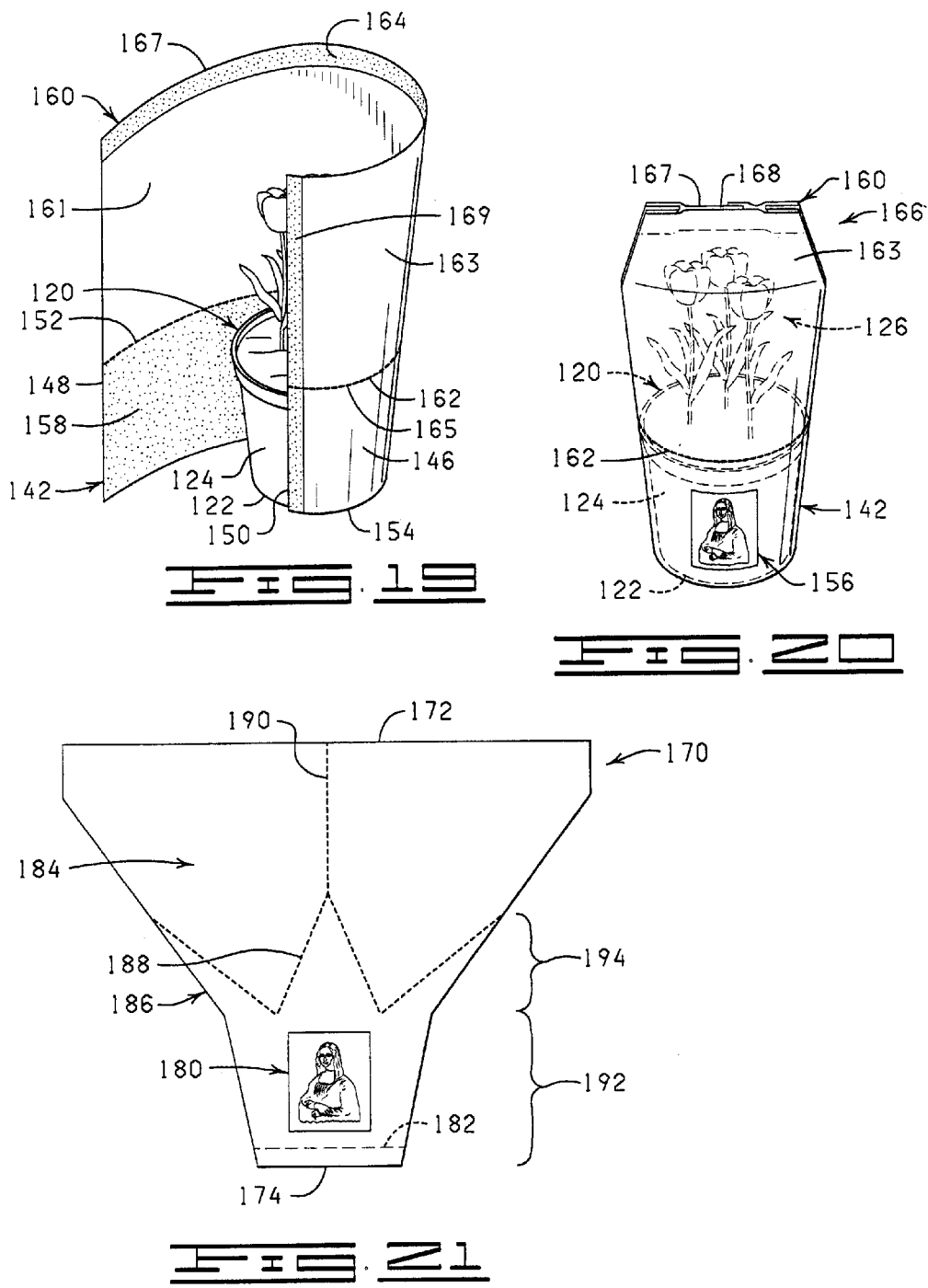

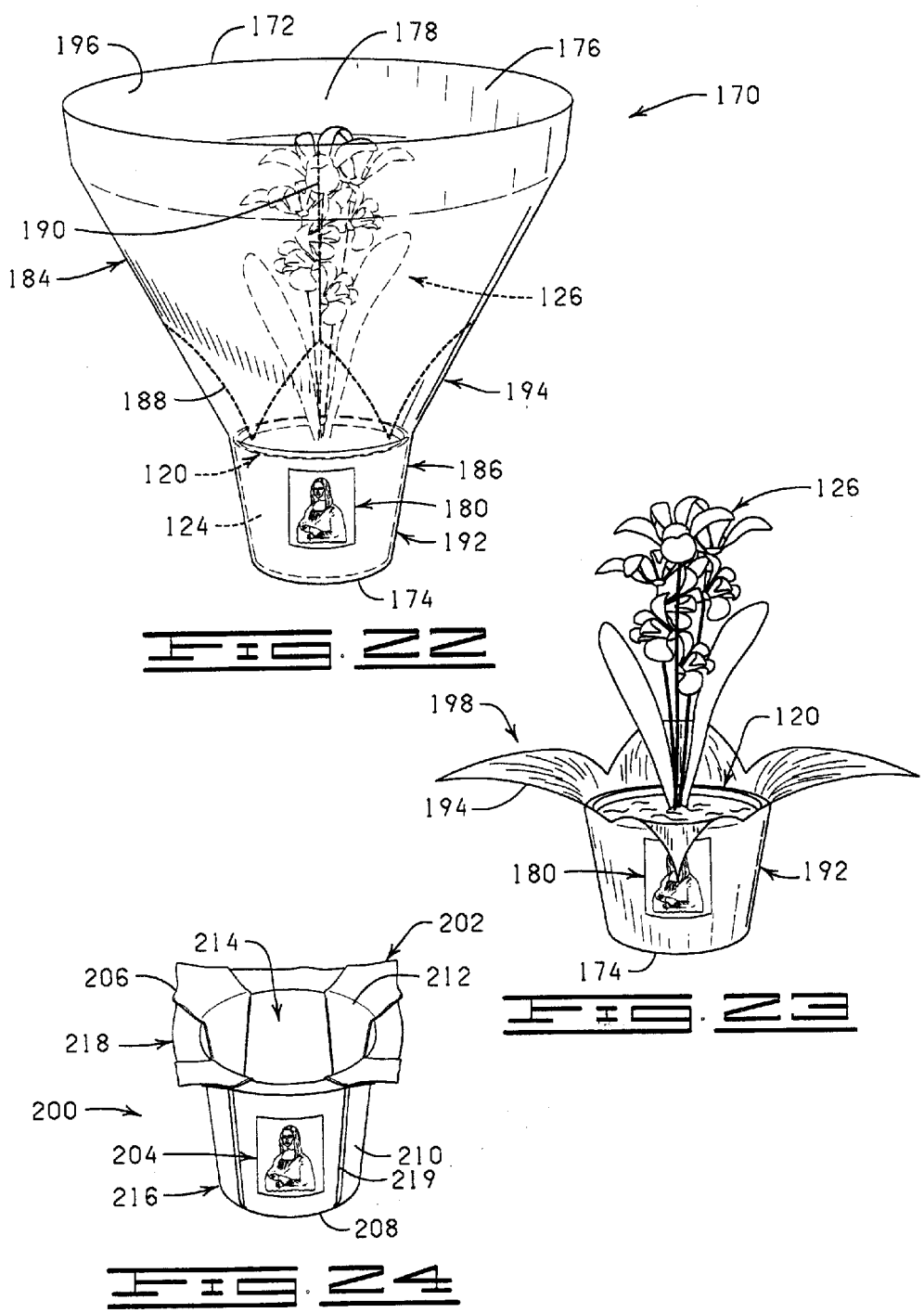

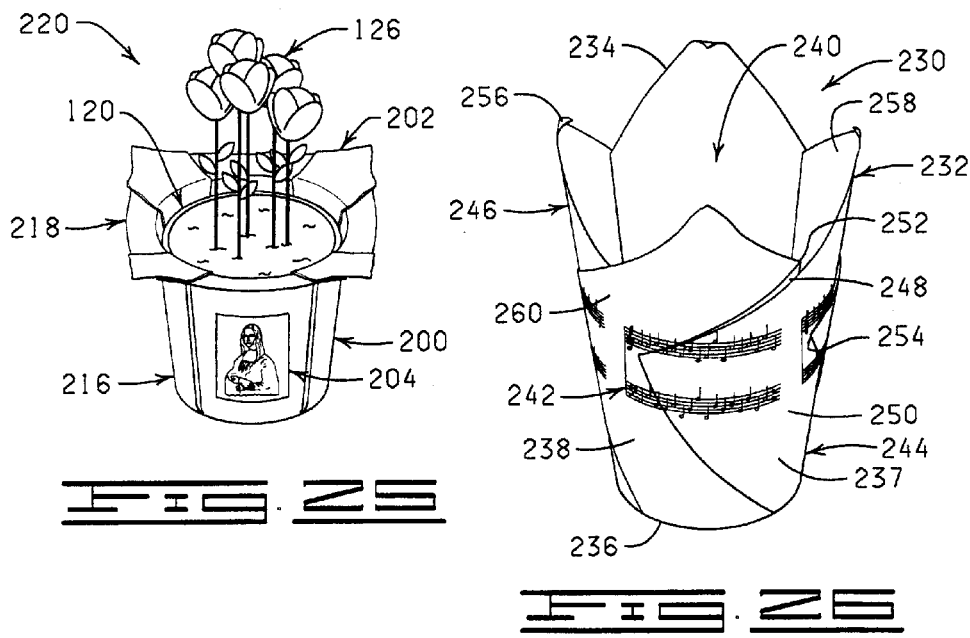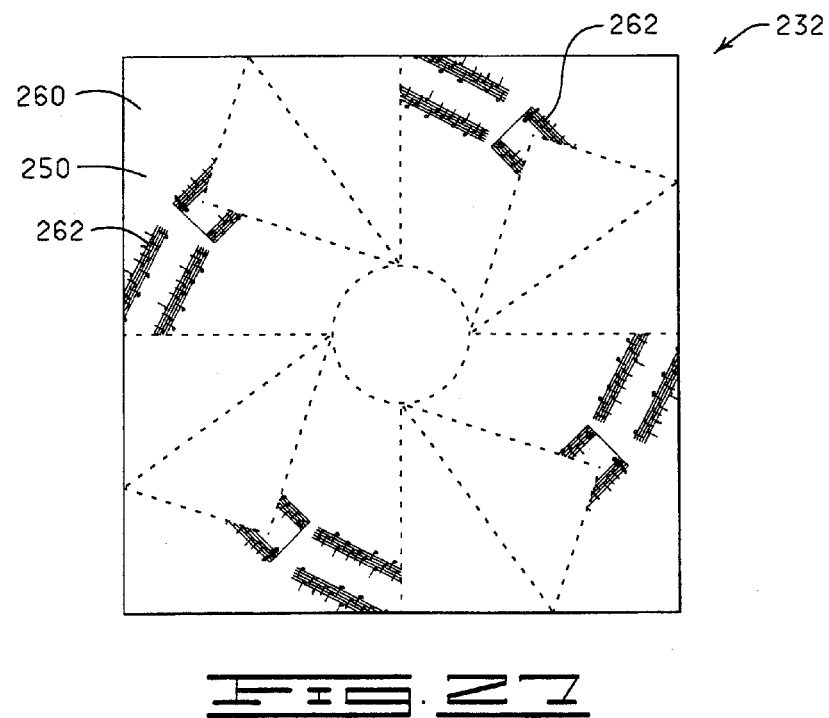

1

FLORAL PACKAGING MATERIAL HAVING GREAT MASTERS PRINTS THEREON

CROSS-REFERENCE TO RELATED APPLICATIONS

This application is a continuation of U.S. Ser. No. 09/643,482, filed Aug. 22, 2000, now U.S. Pat. No. 6,510,650, issued Jan. 28, 2003; which is a continuation-in-part of U.S. Ser. No. 09/151,789, filed Sep. 11, 1998, now abandoned; which is a continuation-in-part of U.S. Ser. No. 08/967,706, filed Nov. 10, 1997, now U.S. Pat. No. 5,839,255, issued Nov. 24, 1998; which is a continuation of U.S. Ser. No. 08/821,012, filed Mar. 19, 1997, now U.S. Pat. No. 5,720,152, issued Feb. 24, 1998; which is a divisional of U.S. Ser. No. 08/477,003, filed Jun. 7, 1995, now U.S. Pat. No. 5,661,951, issued Sep. 2, 1997.

FIELD OF THE INVENTION

The present invention relates generally to the field of packaging materials, and more particularly but not by way of limitation, to a decorative packaging material for floral groupings.

SUMMARY OF THE INVENTION

The present invention provides an apparatus and a method for decoratively covering floral groupings. A sheet of material is provided that is suitable for packaging the floral grouping, the sheet of material being provided with a graphic image such as a masterpiece work of art or a musical score. The sheet of material is fashioned into a decorative covering for the floral grouping in a manner such that the graphic image is conspicuously displayed in order to enhance the decor of the floral grouping. By selecting a particular graphic image, such as a particular masterpiece work of art or a particular musical score that is personally esteemed by the giver or the recipient, then the decorative covering conspicuously bearing such graphic image can lend transcendent meaning and thereby enhance the value of the floral grouping when given as a gift or used as a decoration.

These and other advantages and features of the present invention will be apparent to one of ordinary skill in the art from the following description when read in conjunction with the drawings and appended claims.

BRIEF DESCRIPTION OF THE DRAWINGS

FIG. 1 is a pictorial plan view representing a sheet of material having a graphic illustration of a masterpiece work of art constructed in accordance with the present invention.

FIG. 2 is a cross-sectional view of the sheet of material of FIG. 1 taken along line 2—2.

FIG. 3 is a pictorial plan view representing a sheet of material similar to the sheet of material of FIG. 1 but having an alternative graphic illustration of a musical score.

FIG. 4 is a perspective representation of a sheet of material disposed upon a support surface, the sheet of material having a graphic illustration of a masterpiece work of art thereon and having a bonding material disposed along one edge thereof, one corner of the sheet of material being upwardly turned to show a portion of a lower surface of the sheet of material.

FIG. 5 is a perspective representation of a floral grouping disposed on the sheet of material of FIG. 4.

FIG. 6 is a perspective representation of the floral grouping of FIG. 5 being wrapped with the sheet of material of FIG. 4 by one method of wrapping the sheet of material about the floral grouping.

FIG. 7 is a perspective representation of a decorative cover for a floral grouping formed of the sheet of material of FIG. 4 wherein the decorative cover has a conical configuration.

FIG. 8 is a perspective representation of a decorative cover for a floral grouping formed of the sheet of material of FIG. 4 wherein the decorative cover has a cylindrical configuration.

FIG. 9 is a perspective representation of a floral sleeve provided with a graphic illustration of a masterpiece work of art thereon in accordance with the present invention.

FIG. 10 is a perspective representation of the floral sleeve of FIG. 10 disposed about a floral grouping.

FIG. 11 is a perspective representation of a floral sleeve having a cinching member wherein the floral sleeve is provided with a graphic illustration of a masterpiece work of art thereon.

FIG. 12 is a perspective representation of the floral sleeve of FIG. 11 disposed about a floral grouping.

FIG. 13 is a perspective representation of a pad containing a plurality of sheets of material, wherein each of the sheets of material has a graphic illustration of a masterpiece work of art thereon.

FIGS. 14–16 are perspective representations illustrating sequential steps of a method of wrapping a sheet of material of the pad of FIG. 13 about a flower pot having a floral grouping disposed therein.

FIG. 17 is a perspective representation of a pad containing a plurality of sheets of material, wherein each of the sheets of material has a graphic illustration of a masterpiece work of art and a strip of bonding material thereon.

FIGS. 18–20 are perspective representations illustrating sequential steps of a method of wrapping a sheet of material of the pad of FIG. 17 about a flower pot having a floral grouping disposed therein.

FIG. 21 is an elevational representation of a floral sleeve having a detachable upper portion wherein the sleeve is provided with a graphic illustration of a masterpiece work of art thereon.

FIG. 22 is a perspective representation of the floral sleeve of FIG. 21 having a flower pot containing a floral grouping disposed therein.

FIG. 23 is perspective representation of a flower pot disposed in the floral sleeve of FIG. 21 wherein the upper portion of the floral sleeve has been removed to provide a decorative covering having a skirt portion extending decoratively about a portion of the floral grouping.

FIG. 24 is a perspective representation of a preformed pot cover formed from a sheet of material having a graphic illustration of a masterpiece work of art thereon.

FIG. 25 is a perspective representation of the preformed pot cover of FIG. 24 having a flower pot containing a floral grouping disposed therein.

FIG. 26 is a perspective representation of a preformed pot cover formed from a sheet of material having a graphic illustration of a musical score thereon.

FIG. 27 is a pictorial plan view representing a sheet of material having a graphic illustration of a musical score constructed in accordance with the present invention.

DETAILED DESCRIPTION OF THE INVENTION

Description of FIGS. 1–3

Referring now to the drawings, shown in FIGS. 1 and 2 is a sheet of material 10 having an upper surface 12, a lower surface 14, a first side 16, a second side 18, a first end 20, and a second end 22. The sheet of material 10 is generally square or rectangular shaped; however, the sheet of material 10 could be circularly shaped or have any other configuration desired in a particular application.

The sheet of material 10 is a relatively thin sheet of flexible, foldable material. The thickness of the sheet of material 10 may vary as long as the sheet of material 10 retains sufficient flexibility and foldability so that the sheet of material 10 can be easily formed into a decorative covering for a floral grouping, a decorative covering for a flower pot, or a sleeve which can be disposed about a floral grouping or a flower pot. Desirably, however, the sheet of material 10 is provided with a thickness in a range of from about 0.1 mil to about 30 mil. The sheet of material 10 can be constructed of any suitable material such as paper, foil, polymeric film, metallized film, cloth, laminates thereof and combinations thereof.

The term "polymeric film" as used herein includes synthetic materials such as polypropylene, and naturally occurring materials such as cellophane. A polymeric film is relatively strong and not as readily subject to tearing (substantially non-tearable when used to cover portions of an object) as might be paper or foil.

A decorative background pattern such as a solid color, a printed pattern, and/or an embossed pattern can be applied to the sheet of material 10, or the sheet of material 10 can be provided with a matte or textured finish simulating the appearance of cloth or paper. Additionally, a graphic image 24 is provided on at least a selected portion of one of the upper and lower surfaces 12 and 14 of the sheet of material 10 so as to be conspicuously and prominently displayed when the sheet of material 10 is put to its intended use, as is discussed herein below. The graphic image 24 can be printed directly on the lower surface 14 of the sheet of material 10, or alternatively printed as a reversed image on the upper surface 12 of the sheet of material 10 if the sheet of material 10 is substantially transparent, or printed as a combination on both the upper and lower surfaces 12 and 14 of the sheet of material 10, thereby providing a three-dimensional effect.

The graphic image 24 can be a rendering of at least a portion of a masterpiece work of art. A "masterpiece work of art" is defined herein as any product of one of the fine arts, such as a painting or a photograph, that is widely recognizable by the public and can generally be said to provide aesthetic satisfaction to the viewer. The term "masterpiece work of art" as used herein includes works by deceased artists, such as Leonardo da Vinci, Claude Monet or Norman Rockwell, as well as works by living artists that are currently recognizable, such as Thomas Kincade, Glynda Turley, Marilyn Hageman, Ansel Adams, Anne Geddes and Kim Anderson. The term "rendering of at least a portion of a masterpiece work of art" not only includes exact reproductions of an original work but will also include reproductions and partial reproductions that resemble an original masterpiece work of art, such as a forgery or an imitation, works that contain an adoption of a general style of artistic expression that is recognizable, such as the Impressionist style of painting, and works that include alterations to a famous work, such as a negative image of a work, a change in coloration of a work, or the addition of a person, object or logo to a work.

In addition, the graphic image 24 can be selected from any of a number of works of art commonly associated with the work of the Great Masters. The term "works of the Great Masters" is to be understood to mean a work of art produced by an artist generally associated with at least one of the historical periods or movements, such as but not limited to, the Renaissance period, the Baroque period, the Rococo period, the Abstract period, the Victorian period, and movements such as Impressionism, Classicism, Neoclassicism, Romanticism, Symbolism, Realism, Expressionism, Gothicism, Minimalism, Modernism, Fauvism, Cubism, Surrealism, Precisionism, Art Deco, Art Nouveau, Arts and Crafts and the like. Examples of such artists includes but are not limited to Fra Angelico, Botticelli, Donatello, Ghiberti, Ghirlandaio, Giotto, Filippino, Lippi, Mantegna, Masaccio, Perugino, Piero della Francesca, Pollaiuolo, Signorelli, Verrocchio, Andrea del Sarto, Fra Bartolommeo, Leonardo, Michelangelo, Raphael, Titian, Altdorfer, Durer, Elsheimer, Grunewald, Mabuse, Massys, Van der Weyden, Rembrandt, Henri, Delacroix, Gauguin, Chagall, Rubens, Goya, Van Gogh, Velasquez, Carracci, Carravaggio, Ribalta, Ribera, Vermeer, Cassatt, Cezanne, Degas, Monet, Manet, Renoir, Pissarro, Sisley, Toulouse-Lautrec, Rousseau, Watteau, Boucher, Tiepolo, Chardin, David, Pannini, Ingres, Mengs, Corot, Millet, Thomas Eakins, Henry Tanner, Turner, Friedrich, Constable, Blake, Alma-Tadema, Godward, Leighton, Rossetti, Millias, Hunt, Gericault, Moreau, Redon, de Chavannes, Beardsley, Tiffany, William Morris, Edvard Munch, Franz von Stuck, Kandinsky, Macke, Matisse, Picasso, Klee, Grosz, Francis Bacon, Norman Rockwell, Jackson Pollack, Salvador Dali, Georgia O'Keefe, Andy Warhol and the like.

It will be understood that the graphic image 24 may be a depiction of at least a portion of a musical score, as described in more detail hereinbelow, or the graphic image 24 may be a combination of at least a portion of a masterpiece work of art and at least a portion of a musical score.

The decorative coverings of the present invention supplement the transcendent value of a potted plant or floral grouping disposed therein, and it is this synergistic combination of art and floral grouping to which the present invention is aimed. By providing the sheet of material 10 and selectively applying the graphic image 24 to the sheet of material 10, the sheet of material 10 can be used in any of a number of ways to decoratively wrap a floral grouping or provide a decorative covering for a flower pot in accordance with the present invention.

A bonding material 26 is disposed on at least a portion of the upper surface 12 of the sheet of material 10. However, it will be understood that the bonding material 26 may alternatively be disposed on at least a portion of the lower surface 14 of the sheet of material 10 or on at least a portion of both the upper and lower surfaces 12 and 14 of the sheet of material 10. The term "bonding material" as used herein includes adhesives, such as pressure sensitive adhesives, and cohesives. Where the bonding material 26 is a cohesive, a cohesive material is placed on portions of the sheet of material 10 which will bondingly contact and bondingly engage the cohesive bonding material 26. For example, the sheet of material 10 may be provided with a cohesive binding material 26 on at least a portion of both the upper and lower surfaces 12 and 14 thereof, and the sheet of material 10 may be secured about a floral grouping or a potted plant by bondingly connecting the bonding material 26 disposed on the upper surface 12 of the sheet of material 10 to the bonding material 26 disposed on the lower surface 14 of the sheet of material 10.

The term "bonding material" also includes materials which are heat sealable. The term "bonding material" as used herein also means a lacquer, which may be applied to the sheet of material 10 and, in this instance, heat, sound waves, or vibrations also must be applied to effect the sealing of the lacquer. The bonding material 26 may also be tinted or colored by using a dye, pigment or ink. U.S. Pat. No. 5,147,706 entitled "Water Based Ink On Foil And/Or Synthetic Organic Polymer" issued to Kingman on Sep. 15, 1992 and hereby expressly incorporated herein by reference, provides one water based ink which may be used to tint the bonding material 26.

The tack level of the bonding material 26 should be controlled in most applications so that the sheet of material 10 does not destroy or substantially damage the object bonded thereto when removed from the object, or does not destroy any decorative pattern or the graphic image 24 which is applied to the upper surface 12 or lower surface 14 of the sheet of material 10.

As stated above, in addition to the works of the Great Masters, other graphic images are likewise capable of enhancing the transcendent value of a floral grouping and are likewise contemplated as being within the scope of the present invention.

Shown in FIG. 3 is another version of a sheet of material designated by the reference numeral 10i awhich is similar to the sheet of material 10 described herein before with reference to FIG. 1, except as described herein below. The sheet of material 10a is provided with an upper surface 12a, a lower surface 14a, a first side 16a, a second side 18a, a first end 20a and a second end 22a. The sheet of material 10a is provided with graphic image 24a which is a depiction of a particular musical score on at least a portion of one of the upper and lower surfaces 12a and 14a thereof. The term "musical score" is understood to refer to the diagrammatic rendering of a well known musical composition, set forth as notes placed upon the bass and/or treble clefts and so arranged to define the order, combination, and duration with which individual notes are to be played in order to provide the associated musical composition. The sheet of material 10a bearing the graphic image 24a as illustrated in FIG. 3 falls within the scope of the present invention wherein the synergistic effect of the musical score of the graphic image 24a in combination with a floral grouping or a potted plant provides a transcendent value exceeding the sum of the graphic image 24a and the floral grouping or potted plant separately.

While the graphic image 24a is depicted as a musical score in FIG. 3, it will be understood that the graphic image 24a may be a combination of at least a portion of a masterpiece work of art and at least a portion of a musical score.

Description of FIGS. 4–8

Turning now to FIG. 4, a sheet of material 30 constructed in accordance with the present invention is illustrated. The sheet of material 30 is similar to the sheets of material 10 and 10a described herein above with reference to FIGS. 1 and 3, except as described below. The sheet of material 30 has an upper surface 32, a lower surface 34, a first side 36, a second side 38, a first end 40, a second end 42 and a bonding material 44 provided over only a portion of the upper surface 32 of the sheet of material 30, such as a strip of bonding material 44 disposed substantially adjacent the second side 38 of the sheet of material 30. As previously described for the sheet of material 10, the sheet of material 30 can have a background color or pattern (not shown), which can be printed on the sheet of material 30 randomly. The sheet of material 30 is also provided with a graphic image 46 printed at a particular location and at a particular orientation on at least a portion of the sheet of material 30 so that the graphic image 46 is prominently displayed so as to enhance the decor of a floral grouping when the sheet of material 30 is disposed about a floral grouping. The graphic image 46 is similar to the graphic images 24 and 24a of the sheets of material 10 and 10a of FIGS. 1 and 3, respectively. In FIG. 4, the graphic image 46 is depicted as being a masterpiece work of art. However, it will be understood that the graphic image 46 may be at least a portion of a masterpiece work of art, at least a portion of a musical score, or a combination thereof.

A floral grouping 50 is diagrammatically shown in FIG. 5, the floral grouping 50 generally having a stem portion 52 and a bloom portion 54. The term "floral grouping" as used herein refers to arrangements of cut, fresh flowers, artificial flowers and other fresh and/or artificial flowers, and fresh and/or artificial plants, and such arrangements may include other secondary plants which add to the aesthetics of the overall floral grouping 50.

FIGS. 5–7 illustrate the sheet of material 30 being wrapped about the floral grouping 50. It will be understood that the sheets of material 10 or 10a shown in FIGS. 1 and 3, respectively, may be utilized in a similar manner. However, for the sake of brevity, only the use of the sheet of material 30 to wrap the floral grouping 50 will be described in detail herein after. The sheet of material 30 is disposed upon a support surface 56, and the floral grouping 50 is disposed on the upper surface 32 of the sheet of material 30 as shown in FIG. 5 such that the floral grouping 50 is disposed in a diagonal orientation on the sheet of material 30.

The sheet of material 30 is wrapped about the floral grouping 50 by overlapping a portion of the sheet of material 30 over another portion of the sheet of material 30. That is, for example, the second end 42 of the sheet of material 30 is placed over the floral grouping 50, as shown in FIG. 6. The floral grouping 50 is rolled in the direction toward the second side 38 until the upper surface 32 of the sheet of material 30 near the second side 38 thereof engages the lower surface 34 of the sheet of material 30, wherein the floral grouping 50 is substantially encompassed by the sheet of material 30, and the bonding material 44 disposed on the upper surface 32 of the sheet of material 30 comes into contact with the lower surface 34 of the sheet of material 30, thereby forming a decorative covering 58 which is conically-shaped, as illustrated in FIG. 7. Thus, the bloom portion 54 of the floral grouping 50 is disposed adjacent an open upper end 60 of the decorative covering 58, while the stem portion 52 of the floral grouping 50 is disposed adjacent a lower end 62 of the decorative covering 58. The graphic image 46 is prominently displayed on a selected portion of the decorative cover 54.

FIG. 8 illustrates an alternative method of wrapping the floral grouping 50 in the sheet of material 30 to provide a decorative covering 58a which is cylindrically-shaped. The floral grouping 50 is disposed upon the sheet of material 30 substantially parallel to the first side 36 of the sheet of material 30. The sheet of material 30 is wrapped generally about the stem portion 52 and the bloom portion 54 of the floral grouping 50 in a manner so as to keep first side 36 of the sheet of material 30 substantially parallel to the second side 38 of the sheet of material 30. As the floral grouping 50 is continued rolled, the first side 36 of the sheet of material 30 overlaps the opposing second side 38 thereof in a cylindrical fashion to provide the cylindrically shaped decorative wrapper 58a having an open upper end 60a and a lower end 62a. The graphic image 46 is prominently displayed on a selected portion of the decorative covering 58a.

The decorative coverings 58 and 58a formed from the sheet of material 30 in the manner described above function under ordinary handling conditions to substantially prevent damage to the floral grouping 50 disposed therein. Such damage can be, for example, crushing, breaking, bending, or bruising of the petals of the flowers of the bloom portion 54 of the floral grouping 50. By ordinary handling conditions it is meant the manner typically employed in the floral industry to wrap floral groupings for storage, shipping or sale.

Description of FIGS. 9–12

Shown in FIG. 9 is a flexible sleeve 70 having an open upper end 72, an open lower end 74, an outer peripheral surface 76 and an inner peripheral surface 78 which defines a retaining space 80. A graphic image 82 is provided on at least a portion of the outer peripheral surface 76 of the sleeve 70. In FIG. 9, the graphic image 82 is depicted as being a masterpiece work of art. However, it will be understood that the graphic image 82 may be at least a portion of a musical score alone or in combination with at least a portion of a masterpiece work of art.

The sleeve 70 is generally conically shaped and tapered outwardly from the lower end 74 toward a larger diameter at the open upper end 72 thereof. However, it is to be understood that the sleeve 70 can be, for example, cylindrical, frusto-conical, a combination of both frusto-conical and cylindrical, or any other shape, whether geometric, non-geometric, asymmetrical and/or fanciful, as long as it functions in accordance with the present invention.

FIG. 10 illustrates the floral grouping 50 disposed within the retaining space 80 of the sleeve 70, thereby forming a decorative covering 84 for the floral grouping 50. The graphic image 82 is prominently displayed on a selected portion of the decorative covering 84. Generally, the bloom portion 54 of the floral grouping 50 is disposed substantially adjacent the open upper end 72 of the sleeve 70 and a portion of the stem portion 52 of the floral grouping 50 extends through the open lower end 74 of the sleeve 70. While the sleeve 70 has been shown herein as having the open lower end 74, it should be understood that the lower end of the sleeve 70 could be closed. In such instance, the stem portion 52 of the floral grouping 50 would be confined in the retaining space 80 of the sleeve 70.

A portion of the sleeve 70 may be crimped about the stem portion 52 of the floral grouping 50 for holding the sleeve 70 about the floral grouping 50, or the sleeve 70 can be crimped and held about the floral grouping 50 by a banding element 86 tied around the sleeve 70, such as is shown in FIG. 10. The step of tying the banding element 86 about a portion of the sleeve 70 results in crimping a portion of the sleeve 70 about the stem portion 52 of the floral grouping 50. While the banding element 86 has been illustrated herein as a string or ribbon, it is to be understood that the banding element 86 can be elastic or non-elastic bands, elastic or non-elastic string, an elastic or non-elastic piece of material, a round piece of material, a flat piece of material, a ribbon, a piece of paper strip, a piece of plastic strip, a piece of wire, a tie wrap, a twist tie or combinations thereof.

However, it will be understood that other methods and elements for crimping the sleeve 70 about the floral grouping 50 can be employed. For example, a sleeve 70a is shown in FIGS. 11 and 12 and is substantially similar to the sleeve 70 described herein before with reference to FIGS. 9 and 10, except that the sleeve 70a is provided with a cinching tab 88 having a bonding material 90 applied to a portion thereof. In a method of use of the sleeve 70a shown in FIGS. 11 and 12, a floral grouping 50 is disposed in the sleeve 70a as described above for disposing the floral grouping 50 in the sleeve 70, and the sleeve 70a is secured thereabout via the cinching tab 88 to form a decorative covering 84a, as shown in FIG. 12. That is, a portion of the sleeve 70a adjacent the cinching tab 88 is crimped about at least a portion of the stem portion 52 of the floral grouping 50 disposed therein, and the cinching tab 88 holds the sleeve 70a in such a position so that the floral grouping 50 is secured therein.

Description of FIGS. 13–16

Referring to FIGS. 13 through 16, illustrated therein is a pad 100 formed from a plurality of sheets of material 102, wherein each of the sheets of material 102 is similar to the sheets of material 10 and 10a described herein previously with respect to FIGS. 1 and 3, except as described hereinbelow. As shown in FIG. 13, each sheet of material 102 has an upper surface 104, a lower surface 106 (FIG. 14), a first side 108, a second side 110, a first end 112 and a second end 114. The upper surface 104 of each sheet of material 102 has a bonding material 116 disposed on at least a portion thereof, wherein the bonding material 116 is substantially similar to the bonding material 26 disposed on the sheet of material 10 as described herein before with reference to FIG. 1. Each of the sheets of material 102 is provided with a graphic image 118. While the graphic image 118 has been illustrated herein as being a masterpiece work of art, it should be understood that the graphic image 118 may be at least a portion of a musical score, alone or in combination with at least a portion of a masterpiece work of art.

As shown in FIG. 14, a flower pot 120 having a lower end 122 and an outer peripheral surface 124 and a floral grouping or plant 126 disposed therein is disposed on the top sheet of material 102 of the pad 100. A portion of the top sheet of material 102 of the pad 100 is separated from the next underlying sheet of material 102 of the pad 100 and wrapped about the flower pot 120. It should be appreciated that the lower surface 106 of the top sheet of material 102 should be substantially non-sticking, or at least releasably sticking, to the bonding material 116 disposed on the upper surface 104 of the adjacently disposed sheet of material 102 in the pad 100. The bonding material 116 may be a cohesive, and will therefore only bond to itself or to another cohesive material. Alternatively, the lower surface 106 of the sheet of material 102 may be rendered non-sticking or releasably sticking by selecting an appropriate foil or polymer film for the lower surface 106 of the sheets of material 102 or coating the lower surface 106 of the sheets of material 102 with wax, or any conventional wax-like substance.

The top sheet of material 102 is wrapped around the outer peripheral surface 124 of the flower pot 120, substantially as shown in FIG. 15. If the bonding material 116 is an adhesive, at least a portion of the bonding material 116 of the sheet of material 102 is placed into adhering contact with at least a portion of the outer peripheral surface 124 of the flower pot 120.

While the sheet of material 102 is being wrapped around and adhesively secured to the flower pot 120, the sheet of material 102 is shaped into a decorative covering 130, substantially as shown in FIG. 16, such that the graphic image 118 is prominently displayed on a selected portion of the decorative covering 130.

The sheet of material 102 is shaped into the decorative covering 130 in such a manner that the portion of the sheet of material 102 containing the graphic image 118 remains substantially undistorted due to the presence of the overlapping folds formed in the decorative covering 130

The decorative covering 130 is provided with a base portion 132 and a skirt portion 134, wherein the base portion 132 of the decorative covering 130 surrounds and encompasses the outer peripheral surface 124 of the flower pot 120 while the skirt portion 134 extends outwardly and downwardly therefrom. However, it should be understood that the skirt portion 134 of the decorative covering 130 could be formed in such a manner that the skirt portion 134 extends outwardly from the base 132 of the decorative covering 130 and surrounds a portion of the floral grouping or plant 126 disposed in the flower pot 120. It should be noted that the bonding material 116 can be disposed on only the portion of the sheet of material 102 which is formed into the base portion 132 of the decorative covering 130 such that the skirt portion 134 of the decorative covering 130 is substantially free of bonding material 116.

Finally, the flower pot 120 and the sheet of material 102, now adhesively secured to the flower pot 120 in the shape of the decorative covering 130, are removed from the pad 100. The pad 100 is then ready for wrapping the new top sheet of material 102 about another flower pot 120.

It should be appreciated that separating the top sheet of material 102 from the pad 100 and wrapping the top sheet of material 102 about the flower pot 120 to form the decorative covering 130 can be performed manually or in an automated fashion. It should also be appreciated that single, separate sheets of material (such as a sheet of material 10 or 10a as shown in FIGS. 1 and 3) or sheets of material dispensed from a continuous roll (not shown) may be used rather than a pad 100 of sheets of material 102.

The steps of the method just described may be varied in a number of ways. For example, the top sheet of material 102 may be completely separated from the pad 100 before the flower pot 120 is disposed upon the sheet of material 102, anytime during the wrapping of the sheet of material 102 about the flower pot 120, or after the formation of the sheet of material 102 into the decorative covering 130 adhesively secured to the flower pot 120.

Description of FIGS. 17–20

With reference to FIGS. 17–20, illustrated therein is a pad 140 containing a plurality of sheets of material 142. As shown in FIG. 17, each sheet of material 142 has an upper surface 144, lower surface 146 (FIG. 19), a first side 148, a second side 150, a first end 152, a second end 154, a graphic image 156 disposed thereon, and a bonding material 158 disposed on at least a portion of the upper surface 144 thereof. Each of the sheets of material 142 is also provided with a sheet extension 160 which extends from the first end 152 of the sheet of material 142 and extends between the first and second sides 148 and 150 of the sheet of material 142 and is detachable therefrom via a detaching element 162, such as a line of perforations, as shown in FIGS. 17–20. The sheet extension 160 is provided with an upper surface 161, a lower surface 163, a lower end 165 congruent with the detaching element 162, and an upper end 167. Further, a strip of bonding material 169 is disposed on the lower surfaces 146 and 163, respectively, of each of the sheets of material 142 and the sheet extension 160 connected thereto. The strip of bonding material 169 is disposed adjacent the second side 150 of the sheet of material 142 and extends between the first and second ends 152 and 154 of the sheet of material 142 and between the upper and lower ends 167 and 165 of the sheet extension 160, substantially as shown in FIG. 19.

The graphic image 156 is printed on at least a portion of at least one of the upper and lower surfaces 144 and 146, respectively, of the sheet of material 142. In FIGS. 17–20, the graphic image 156 is depicted as being a masterpiece work of art. However, it will be understood that the graphic image 156 may be at least a portion of a musical score, alone or in combination with at least a portion of a masterpiece work of art.

The lower surface 146 of each sheet of material 142 can be substantially non-sticking or releasably-sticking with respect to the bonding materials 158 and 169, as described above for the pad 100 containing the plurality of sheets of material 102 shown in FIGS. 13–16. The bonding material 158 is provided on at least a portion of the upper surface 144 of the sheet of material 142 for bondingly connecting the sheet of material 142 to the flower pot 120. The bonding material 169 is provided on the lower surface 146 of the sheet of material 142 and on the lower surface 163 of the sheet extension 160 to join the first and second sides 148 and 150 of the sheet of material 142 in the attachment of the sheet of material 142 about the flower pot 120 and to seal the sheet extension 160 about the floral grouping or plant 126 disposed in the flower pot 120. The sheet extension 160 is also provided with a bonding material 164 disposed on a portion of the upper surface 161 and adjacent the upper end 167 thereof, wherein the bonding material 164 may be an adhesive or cohesive material.

As best illustrated by FIGS. 18 and 19, the top sheet of material 142 of the pad 140 is separated from the pad 140. The separated sheet of material 142 having the sheet extension 160 attached thereto is wrapped about the flower pot 120 with the bonding material 158 adjacent to the outer peripheral surface 124 of the flower pot 120, as shown in FIG. 19. As the sheet of material 142 is disposed around the flower pot 120, at least a portion of the bonding material 158 disposed on the upper surface 144 of the sheet of material 142 is placed in contact with the outer peripheral surface 124 of the flower pot 120 to secure the sheet of material 142 to the flower pot 120.

After the sheet of material 142 is wrapped completely about the flower pot 120, portions of the sheet of material 142 overlap. The bonding material 169 disposed on the lower surface 146 of the overlapping portion of the sheet of material 142 is placed into securing contact with the upper surface 144 of the overlapping portion of the sheet of material 142 to further hold the sheet of material 142 about the flower pot 120 such that the graphic image 156 is prominently displayed. Likewise, the bonding material 169 disposed on the lower surface 163 of an overlapping portion of the sheet extension 160 is placed into securing contact with the upper surface 161 of an overlapping portion of the sheet extension 160 to hold the sheet extension 160 about the floral grouping or plant 126 disposed in the flower pot 120.

Finally, the bonding material 164 disposed on the upper surface 161 of the sheet extension 160 substantially adjacent the upper end 167 thereof connects to itself and, in cooperation with the sheet of material 142, forms a decorative covering 166 having a closed upper end 168 (FIG. 20). The sheet extension 160 can be removed from the decorative covering 166 by tearing along the detaching element 162. The remaining portion of the decorative covering 166 remains adhesively secured to the outer peripheral surface 124 of the flower pot 120.

It should be appreciated that the steps of removing the top sheet of material 142 from the pad 140, wrapping the separated sheet of material 142 about the flower pot 120, and forming the sheet extension 160 about the floral grouping or plant 126 disposed in the flower pot 120 can be performed manually or in an automated fashion. It should also be appreciated that the sheet extension 160 may be substantially transparent for displaying the floral grouping or plant 126 disposed in the flower pot 120.

It will be appreciated that the sheets of material 142 can be provided as single, separate sheets of material (such as the sheets of material 10 or 10a described herein before with reference to FIGS. 1 and 3) or can be dispensed from a continuous roll of sheets of material (not shown) instead of in the pad 140.

Description of FIGS. 21–23

Shown in FIG. 21 is a sleeve 170 fashioned to be disposed about the flower pot 120, the flower pot 120 having been described in detail hereinbefore with reference to FIG. 20. The sleeve 170 has an upper end 172, a closed lower end 174 and an opening 176 (FIG. 22) at the upper end 172 thereof. While the lower end 174 of the sleeve 170 is shown as being closed, it will be understood that the lower end 174 of the sleeve 170 could be open.

Opening the sleeve 170 as shown in FIG. 22 creates an inner retaining space 178 for receiving disposition of the flower pot 120 containing the floral grouping or plant 126. A graphic image 180 is printed on the sleeve 170, and the graphic image 180 is depicted as being at least a portion of a masterpiece work of art. However, it will be understood that the graphic image 180 may be at least a portion of a musical score, alone or in combination with at least a portion of a masterpiece work of art.

A portion of the lower end 174 of the sleeve 170 can be inwardly folded to form one or more gussets 182 (FIG. 21) for permitting the lower end 174 of the sleeve 170 to conform to a circular bottom of the flower pot 120 disposed in the inner retaining space 178 of the sleeve 170. While the sleeve 170 is illustrated with a gusset 182 in the lower end 174 thereof, it is to be understood that the gusset 182 could also be formed in a side portion of the sleeve near the lower end 174 of the sleeve.

As shown in FIG. 21, the sleeve 170 generally has an upper portion 184 and a lower portion 186. The lower portion 186 of the sleeve 170 is generally sized to contain the flower pot 120. The upper portion 184 of the sleeve 170 is sized to substantially surround and encompass the floral grouping or plant 126 that is disposed in the flower pot 120. A detaching element 188, such as a line of perforations, separates the upper and lower portions 184 and 186 of the sleeve 170 to enable a detachment of the upper portion 184 of the sleeve 170 from the lower portion 186 of the sleeve 170. An additional detaching element 190, such as a line of substantially vertically disposed perforations, may also be provided to assist in removal of the upper portion 184 from the lower portion 186 of the sleeve 170.

The lower portion 186 of the sleeve 170 further comprises a base portion 192 and a skirt portion 194. The base portion 192 is that part of the lower portion 186 of the sleeve 170 which, when the flower pot 120 is placed into the lower portion 186, has an inner peripheral surface 196 which is substantially adjacent to and surrounds the outer peripheral surface 124 of the flower pot 120. The skirt portion 194 of the sleeve 170 extends above the flower pot 120 and surrounds at least a portion of the floral grouping or plant 126 disposed in the flower pot 120.

As previously stated, the upper portion 184 of the sleeve 170 is separable from the lower portion 186 of the sleeve 170 by tearing the upper portion 184 away along the detaching elements 188 and 190. Upon removal of the upper portion 184 from the lower portion 186 of the sleeve 170, the base portion 192 surrounds the flower pot 120 and the skirt portion 194 extends from the base portion 192 and surrounds at least a portion of the floral grouping or plant 126, thereby forming a decorative covering 198 for the flower pot 120 having the floral grouping or plant 126 disposed therein, as shown in FIG. 23. The graphic image 180 is prominently displayed on a selected portion of the decorative covering 198.

Description of FIGS. 24–25

FIG. 24 illustrates a preformed flower pot cover 200 formed from a sheet of material 202. The sheet of material 202 is provided with a graphic image 204 disposed on at least a portion thereof, wherein the graphic image 204 is depicted as being a masterpiece work of art. However, it will be understood that the graphic image 204 may be at least a portion of a musical score, alone or in combination with at least a portion of a masterpiece work of art. The graphic image 204 is positioned on the sheet of material 202 such that when the sheet of material 202 is formed into the preformed flower pot cover 200, the graphic image 204 is not concealed and is not substantially distorted by the manner of forming the preformed flower pot cover 200.

The preformed flower pot cover 200 has an upper end 206, a lower end 208, and an outer peripheral surface 210. An opening 212 intersects the upper end 206 of the preformed flower pot cover 200, thereby forming an inner retaining space 214 into which the flower pot 120 can be disposed as shown in FIG. 25. The preformed flower pot cover 200 is provided with a base portion 216 and a skirt portion 218. The base portion 216 of the preformed flower pot cover 200 is sized to substantially surround and encompass the flower pot 120 disposed therein, while the skirt portion 218 extends outwardly and downwardly therefrom. However, it should be understood that the skirt portion 218 of the preformed flower pot cover 200 could be formed in such a manner that the skirt portion 218 extends outwardly from the base portion 216 and surrounds and encompasses at least a portion of the floral grouping or plant 126 disposed in the flower pot 120, wherein the skirt portion 218 is disposed in a position similar to that illustrated and described hereinbefore for the skirt portion 194 of the decorative covering 198 of FIG. 23.

The base portion 216 of the preformed flower pot cover 200 includes a plurality of overlapping folds 219 which are located at predetermined positions on the preformed flower pot cover 200 and incorporate predetermined portions of the sheet of material 202 from which the preformed flower pot cover 200 is formed. The overlapping folds 219 may be connected by any suitable bonding method using any suitable bonding material, such as heat sealing or with an adhesive or cohesive. The overlapping folds 219 of the base portion 216 of the preformed flower pot cover 200 provide structural integrity to the base portion 216 and cooperate to maintain the base portion 216 in the predetermined shape of the preformed flower pot cover 200.

By positioning the overlapping folds 219 at predetermined positions, the portions of the sheet of material 202 incorporated into the overlapping folds 219 can be controlled. In this manner, incorporation of a portion of the graphic image 204 in the overlapping folds 219 of the base portion 216 of the preformed flower pot cover 200 can be prevented, thus preventing or reducing distortion of the graphic image 204. That is, rather than forming overlapping folds at various and random positions on the preformed flower pot cover 200, the positioning and direction of the overlapping folds 219 are controlled to prevent incorporation of the portion of the sheet of material 202 containing the graphic image 204 therein and to prevent concealment or substantial distortion of the graphic image 204 by the overlapping folds 219.

There are various devices and associated methods for forming such a preformed decorative cover 200 as shown in FIG. 24. Such devices and associated methods are described for example in U.S. Pat. No. 5,073,161 entitled "APPARATUS OF MAKING A FLOWER POT OR FLOWER POT COVER WITH CONTROLLED PLEATS" issued to Weder et al on Dec. 17, 1991; U.S. Pat. No. 5,228,934 entitled "METHOD OF FORMING A FLOWER POT OR FLOWER POT COVER WITH CONTROLLED PLEATS" issued to Weder et al on Jul. 20, 1993; and U.S. Pat. No. 5,501,039 entitled "METHOD OF FORMING A FLOWER POT OR FLOWER POT COVER WITH CONTROLLED PLEATS" issued to Weder et al on Mar. 26, 1996, the Specifications of which are all hereby expressly incorporated by reference herein.

In a method of use shown in FIGS. 24 and 25, the flower pot 120 containing a floral grouping or plant 126 is disposed in the inner retaining space 214 of the preformed flower pot cover 200, whereby the preformed flower pot cover 200 provides a decorative covering 220 for the flower pot 120. The base portion 216 of the preformed flower pot cover 200 is substantially adjacent to and surrounds the outer peripheral surface 124 of the flower pot 120, while the skirt portion 218 of the preformed flower pot cover 200 extends from the base portion 216 of the preformed flower pot cover 200 and surrounds a portion of the floral grouping or plant 126 disposed in the flower pot 120 such that the graphic image 204 is prominently displayed on a selected portion of the decorative covering 220.

Description of FIGS. 26 and 27

Shown in FIG. 26 and designated therein by the general reference numeral 230 is another version of a preformed flower pot cover constructed in accordance with the present invention. The preformed flower pot cover 230 is formed of a generally square-shaped, flexible sheet of material 232 shown in FIG. 27. The preformed flower pot cover 230 includes an open upper end 234, a substantially closed lower end 236, a sidewall 237 having an outer peripheral surface 238, and a retaining space 240. The preformed flower pot cover 230 is provided with a graphic image 242 disposed on at least a portion of the outer peripheral surface 238 thereof such that the graphic image 242 is prominently displayed on a selected portion of the preformed flower pot cover 230. The graphic image 242 is illustrated as at least a portion of a musical score. However, it will be understood that the graphic image 242 may be at least a portion of a masterpiece work of art, alone or in combination with at least a portion of a musical score.

The preformed flower pot cover 230 is further characterized as having a base portion 244 and a skirt portion 246. The base portion 244 of the preformed flower pot cover 230 is formed to include a preselected number of overlapping folds 248 and a corresponding number of panel sections 250 which are substantially free of folds, creases and score lines. By forming the panel sections 250 to be substantially free of folds, creases or score lines, the outer surface of each of the panel sections 250 is smooth, and thus the graphic image 242 may be selectively provided on the sheet of material 232 so as to be displayed on the panel sections 250 in such a manner that the graphic image 242 is displayed on the outer peripheral surface 238 of the preformed flower pot cover 230 without being substantially distorted or mutilated by numerous folds or creases.

More specifically, each of the overlapping folds 248 of the base portion 244 include a first fold 252 and a corresponding second fold 254, which cooperate to form a substantially Z-shaped configuration. The first fold 252 is substantially vertically oriented along the length of the sidewall 237 while the second fold 254 is angled relative to the length of the sidewall 237 at an angle ranging from about 5 degrees to about 60 degrees. The overlapping folds 248 provide mechanical strength to the base portion 244 for enabling the base portion 244 to stand upright on the substantially closed lower end 234 of the preformed flower pot cover 230. Thus, the overlapping folds 248 permit relatively thin sheets of material such as films to be utilized to form the preformed flower pot cover 230.

The skirt portion 246 of the preformed flower pot cover 230 includes four petal-like portions, only one of which is designated by the reference numeral 256. Each flared petal-like portion 256 terminates with a pointed end which is formed by one of the four corners of the square-shaped sheet of material 232. Further, each petal-like portion 256 extends a distance upwardly from the base portion 244 terminating with the pointed end of the flared petal-like portion 256.

Referring now to FIG. 27, the sheet of material 232 is characterized as having an upper surface 258 (FIG. 26) and a lower surface 260 (FIG. 27). The lower surface 260 is illustrated as being provided with the graphic image 242 selectively printed on only the portions of the sheet of material 232 which form the panel sections 250 of the preformed flower pot cover 230. In addition, the graphic image 242 is printed on the sheet of material 232 in portions 262 such that one portion 262 will register with another portion 262 upon formation of the preformed flower pot cover 230 whereby the graphic image 242 extends continuously about the outer peripheral surface 238 of the sidewall 237 of the preformed flower pot cover 230, as shown in FIG. 26.

While the graphic image 242 is illustrated as being printed on the sheet of material 232 in portions 262 in FIG. 27, it will be understood that the graphic image 242 may be printed throughout the sheet of material 232 and not only on the portions 262 of the sheet of material 232 which form the panel sections 250 of the preformed flower pot cover 230. However, when the graphic image 242 is printed throughout the sheet of material 232, it is desired that the portions of the graphic image 242 displayed on the outer peripheral surface 238 of the sidewall 237 of the preformed flower pot cover 230 be in register such that the graphic image 242 extends continuously about the outer peripheral surface 238 of the sidewall 237 of the preformed flower pot cover 230. In addition, it will further be understood that the graphic image 242 may be provided only on the portions of the sheet of material 232 which will form the panel sections 250 of the preformed flower pot cover 230 such that the alignment of the graphic image 242 in the area of the second fold 254 of the overlapping folds 248 is not required. Such sheets of material and methods for forming preformed flower pot covers therefrom are disclosed in U.S. Ser. No. 60/206,563 filed May 22, 2000, entitled "FLOWER POT COVER", the Specification of which is hereby expressly incorporated herein by reference.

From the above description, it is clear that the present invention is well adapted to carry out the objects and to attain the advantages mentioned herein as well as those inherent in the invention. While presently preferred embodiments of the invention have been described for purposes of this disclosure, it will be understood that numerous changes may be made which will readily suggest themselves to those skilled in the art and which are accomplished within the spirit of the invention disclosed and as defined in the appended claims.

What is claimed is:

1. A method for forming a decorative covering for a floral grouping, comprising the steps of:

providing a sleeve having an upper end, a lower end, an outer peripheral surface, an opening in the upper end thereof and a retaining space, the sleeve having a graphic image disposed on at least a portion thereof wherein the graphic image is visible on at least a portion of the outer peripheral surface of the sleeve, the graphic image being selected from the group consisting of a rendering of at least a portion of a masterpiece work of art, a rendering of at least a portion of a work of art of a Great Master, a rendering of at least a portion of a musical score and combinations thereof;

providing a floral grouping having a bloom portion and a stem portion;

disposing the floral grouping in the retaining space of the sleeve such that at least a portion of the bloom portion of the floral grouping is disposed adjacent the opening in the upper end of the sleeve and at least a portion of the stem portion of the floral grouping is substantially adjacent the lower end of the sleeve, thereby forming a decorative covering wherein the graphic image is prominently displayed on the decorative covering.

2. The method of claim 1 wherein, in the step of providing the sleeve, the sleeve is constructed of a material selected from the group consisting of paper, polymeric film, foil, combinations thereof and laminations thereof.

3. The method of claim 1 wherein, in the step of providing the sleeve, the sleeve is formed of a material having a thickness in a range of from about 0.1 mil to about 30 mil.

4. The method of claim 1 further comprising the step of cinching a portion of the sleeve about the stem portion of the floral grouping to secure the sleeve about the floral grouping.

5. The method of claim 4 wherein the sleeve is provided with a banding element for bondingly securing the sleeve in a cinched position about the stem portion of the floral grouping.

6. A method for forming a sheet of material about a flower pot to provide a decorative covering comprising the steps of:

providing a sheet of material having an upper surface and a lower surface, the sheet of material having a graphic image disposed on at least a portion of at least one of the upper and lower surfaces of the sheet of material, the graphic image being selected from the group consisting of a rendering of at least a portion of a masterpiece work of art, a rendering of at least a portion of a work of art of a Great Master, a rendering of at least a portion of a musical score and combinations thereof;

providing a flower pot having a lower end and an outer peripheral surface;

placing the lower end of the flower pot on the sheet of material; and forming the sheet of material about the outer peripheral surface of the flower pot to provide the decorative covering having overlapping folds formed therein, whereby the graphic image of the sheet of material is prominently displayed on the decorative covering and remains substantially undistorted by the presence of the overlapping folds in the decorative covering.

7. The method of claim 6 wherein, in the step of providing the sheet of material, the sheet of material is provided with a bonding material disposed on at least a portion of at least one of the upper and lower surfaces thereof, the bonding material pressingly engaging the outer peripheral surface of the flower pot to attach the sheet of material to the flower pot.

8. The method of claim 6 wherein, in the step of providing the sheet of material, the sheet of material is constructed of a material selected from the group consisting of paper, foil, polymeric film, laminations thereof and combinations thereof.

9. The method of claim 6 wherein, in the step of providing the sheet of material, the sheet of material is defined further as having a thickness in a range of from about 0.1 mil to about 30 mil.

10. A method for forming a sheet of material about a flower pot to provide a decorative covering comprising the steps of:

providing a sheet of material having an upper surface, a lower surface and a sheet extension detachably connected thereto via a detaching element, the sheet of material being provided with a graphic image disposed on at least a portion of at least one of the upper and lower surfaces thereof and a bonding material disposed on at least a portion of the upper surface thereof, the graphic image being selected from the group consisting of a rendering of at least a portion of a masterpiece work of art, a rendering of at least a portion of a work of art of a Great Master, a rendering of at least a portion of a musical score and combinations thereof;

providing a flower pot having a lower end and an outer peripheral surface, the flower pot having a floral grouping disposed therein; and forming the sheet of material about the outer peripheral surface of the flower pot to provide the decorative covering whereby the graphic image of the sheet of material is prominently displayed on the decorative covering, the bonding material bondingly connecting the sheet of material to the outer peripheral surface of the flower pot such that the sheet of material is secured to the flower pot, and the sheet extension being formed about the floral grouping disposed in the flower pot.

11. The method of claim 10 wherein, in the step of providing the sheet of material, the sheet of material is constructed of a material selected from the group consisting of paper, foil, polymeric film, laminations thereof and combinations thereof.

12. The method of claim 10 wherein, in the step of providing the sheet of material, the sheet of material is defined further as having a thickness in a range of from about 0.1 mil to about 30 mil.

13. A method for decoratively covering a flower pot, comprising the steps of:

providing a preformed flower pot cover having an upper end, a lower end, an outer peripheral surface, a retaining space, and having controlled pleats formed therein and a graphic image which is substantially undistorted and visible on the outer peripheral surface thereof, the graphic image being selected from the group consisting of a rendering of at least a portion of a masterpiece work of art, a rendering of at least a portion of a work of art of a Great Master, a rendering of at least a portion of a musical score and combinations thereof;

providing a flower pot having a lower end and an outer peripheral surface, the flower pot having a floral grouping disposed therein; and disposing the flower pot in the retaining space of the preformed flower pot cover whereby the graphic image is prominently displayed.

14. The method of claim 13 wherein, in the step of providing the preformed flower pot cover, the preformed flower pot cover is constructed of a material selected from the group consisting of paper, polymeric film, foil, combinations thereof and laminations thereof.

15. The method of claim 13 wherein, in the step of providing the preformed flower pot cover, the preformed flower pot cover is formed of a material having a thickness in a range of from about 0.1 mil to about 30 mil.

* * * * *